United States Patent [19]

Fiato

[11] 4,233,466
[45] Nov. 11, 1980

[54] HOMOLOGATION PROCESS FOR THE PRODUCTION OF ETHANOL FROM METHANOL

[75] Inventor: Rocco A. Fiato, Charleston, W. Va.

[73] Assignee: Union Carbide Corporation, New York, N.Y.

[21] Appl. No.: 91,241

[22] Filed: Nov. 15, 1979

[51] Int. Cl.$^3$ .............................................. C07C 29/32
[52] U.S. Cl. ................................ 568/902; 252/429 R; 252/431 C; 252/431 P
[58] Field of Search .......................................... 568/902

[56] References Cited
U.S. PATENT DOCUMENTS

| | | | |
|---|---|---|---|
| 3,248,432 | 4/1966 | Riley et al. | 568/902 |
| 3,285,948 | 11/1966 | Butter | 568/902 |
| 4,133,966 | 1/1979 | Pretzer et al. | 568/902 |

*Primary Examiner*—Joseph E. Evans
*Attorney, Agent, or Firm*—Stanley Ktorides

[57] ABSTRACT

A process for producing ethanol from the reaction of methanol, hydrogen and carbon monoxide catalyzed by a phosphine-iodine promoted cobalt-ruthenium catalyst, the improvement of maintaining the phosphine to halide ratio and concentration within a critical range, and whereby the concentration of phosphine compound in the reaction mixture is increased without causing an undesirable decrease in the activity of the catalyst; thereby obtaining a highly stable and active catalyst providing an increased selectivity to ethanol formation. This is accomplished under such conditions that the catalyst stability is maintained and the ratio of phosphine to halide is kept at a relatively constant value during the reaction.

12 Claims, No Drawings

HOMOLOGATION PROCESS FOR THE PRODUCTION OF ETHANOL FROM METHANOL

BACKGROUND OF THE INVENTION

As the price of petroleum continues to increase and as the availability of petroleum becomes more questionable ethanol is becoming increasingly more important as a source for hydrocarbon-based fuels and chemicals. Ethanol has long been produced by the well known fermentation process. Another more recent process of producing ethanol is the reaction of methanol with hydrogen and carbon monoxide (syn gas). This method has significant advantages because relatively inexpensive reactants are employed; however, it requires a catalyst for commercially viability. Therefore, there has been much attention given to the development of better catalysts for this very important reaction.

There are basically three significant and important parameters or criteria by which catalysts are judged: stability, activity, and selectivity. Stability relates to how long the catalyst remains functional before breaking down; activity relates to the amount of reactants the catalyst can convert per unit time; selectivity relates to the amount of desired product as opposed to undesired products that the catalyzed reaction forms. Generally catalysts that increase one of the parameters tend to have a detrimental effect on another of these parameters with the result that whenever any one of the other parameters is decreased the yield of desired product from the reaction generally suffers.

It has long been known that a water soluble cobalt catalyst and an iodine promoter will catalyze the reaction of methanol, hydrogen and carbon monoxide to produce ethanol. However, this catalyst system has often been characterized with low ethanol yields due to poor selectivity. There have been many attempts to improve this basic catalyst system. For example, U.S. Pat. No. 3,248,432 discloses the introduction of a phosphorus compound soluble in methanol to the basic catalyst system; U.S. Pat. No. 3,285,948 discloses the use of halides of ruthenium or osmium as second promoters in combination with the basic cobalt and iodine catalyst system; Netherlands Pat. No. 7606138 discloses the use of tertiary phosphines and nonpolar solvents in addition to the basic cobalt/iodide catalyst system and further states that the nonpolar solvent is crucial to the attainment of the high selectivity reported; and U.S. Pat. No. 4,133,966 discloses a four component catalyst system composed of cobalt acetylacetonate, a tertiary organo Group VA compound, an iodine promoter and, as a second promoter, a ruthenium compound.

It is known that the selectivity of the reaction of methanol, hydrogen and carbon monoxide to ethanol can be increased by increasing the mole ratio of hydrogen to carbon monoxide; unfortunately this increase in the mole ratio results in poor catalyst stability as the cobalt tends to precipitate out as the metal. It is also general knowledge that the stability problem can be overcome to some extent by the use of a tertiary organo Group VA ligand. This use is shown, for example, in U.S. Pat. No. 4,133,966; however, this has created another problem for as one increases the level of the tertiary phosphorus compound in relation to the other catalyst components, the activity of the catalyst is decreased. This limits the total yield of ethanol which can be obtained. A method which can allow the use of higher amounts of Group V ligands without harming catalyst activity so that catalyst stability can remain high even though the hydrogen to carbon monoxide mole ratio is increased for purposes of higher selectivity, would be advantageous.

SUMMARY OF THE INVENTION

It has now been found that in the reaction of methanol, hydrogen and carbon monoxide to selectively form ethanol wherein the reaction is catalyzed by a four component system containing cobalt, ruthenium, an iodine compound and an organic phosphine, the amount of organic phosphine in the reaction mixture can be increased to concentrations heretofore unachievable without severe loss of catalyst activity; this has been accomplished by increasing the concentration of phosphine compound in conjunction with the concentration of total halide such that the mole ratio and concentration of phosphine to halide are maintained within a critical range. This novel method allows the use of higher hydrogen to carbon monoxide mole ratios, thereby increasing selectivity, without the heretofore unavoidable deleterious effect on catalyst stability. The high selectivity to ethanol is obtained without the need for a nonpolar cosolvent.

DESCRIPTION OF THE INVENTION

This invention is an improved catalytic method for selectively producing ethanol from methanol, hydrogen and carbon monoxide. Furthermore, any compounds which will form hydrogen and carbon monoxide, such as the mixture of water and carbon monoxide or the mixture of hydrogen and carbon dioxide, can be used as a substitute for the mixture of hydrogen and carbon monoxide used herein to exemplify the present invention.

The catalyst system for the improved process of this invention is comprised of four components: (1) cobalt, (2) ruthenium, (3) an iodine compound and (4) an organic phosphine.

The cobalt component of the catalyst can come from a number of sources such as any of known cobalt carboxylates such as cobalt formate, cobalt acetate, cobalt propionate, cobalt butyrate, cobalt valerate, cobalt hexanoate, and the like; the known cobalt carbonyl compounds such as dicobalt octacarbonyl, methyl cobalt tetracarbonyl, acetyl cobalt tetracarbonyl, and the like, or their phosphine substituted analogs many of which are known to those skilled in the art; cobalt oxide and cobalt hydroxide; cobalt carbonate and cobalt bicarbonate; and the soluble cobalt halides such as cobalt iodide, cobalt bromide and cobalt chloride. A convenient source of cobalt is cobalt acetate.

Although many soluble halides may be used as a promoter in the catalyst system it is preferred that iodine or its derivatives be so employed. Illustrative as sources of the iodide atom are elemental iodine; cobalt iodide; hydrogen iodide; the alkyl iodides having from 1 to 10 carbon atoms such as methyl iodide, ethyl iodide, propyl iodide, 2-ethyhexyl iodide, n-decyl iodide, and the like. Any other source of iodide which will ionize to form free iodide ions in the reaction medium can be used as promoter. One can also employ any of the organic iodine compounds that will furnish iodide to the reaction medium. Further, one can use mixtures of iodine and/or iodide compounds, if so desired. The preferred source of the iodide is elemental iodine.

The ruthenium which is used in the four component catalyst system can come from any source which is capable of providing soluble ruthenium atoms in the reaction. Illustrative of such ruthenium compounds one can name ruthenium trichloride, ruthenium tribromide, ruthenium triiodide, ruthenium acetate, ruthenium acetylacetonate, ruthenium propionate, ruthenium octanoate, ruthenium dioxide, ruthenium tetraoxide, ruthenium pentacarbonyl, triruthenium dodecacarbonyl and the like. Convenient sources of ruthenium are ruthenium trichloride and triruthenium dodecacarbonyl.

The organic phosphines which are employed in the four component catalyst system are the phosphines of the formula

wherein $R_1$, $R_2$, and $R_3$, are individually monovalent organic radicals which either can be dissimilar or any two can be similar or all three can be similar or any two taken together can form an organic divalent cyclic ring system.

The $R_1$, $R_2$, and $R_3$ groups are alkyl, saturated or unsaturated, linear or branched, having from 1 to 20 carbon atoms, preferably from 4 to 10 carbon atoms; or aryl, aralkyl or alkaryl having from 6 to 10 ring carbon atoms preferably 6 ring carbon atoms; or cycloalkyl having from 5 to 8 ring carbon atoms, preferably 6 ring carbon atoms. Illustrative of phosphines suitable for use in the catalyst system one can name triethylphosphine, tributylphosphine, triphenylphosphine, tri(4-methoxyphenyl)phosphine, tris(4-tolyol)phosphine, tris(3-chlorophenyl)phosphine, diphenylhexylphosphine, dimethyl(3-methoxyphenyl)phosphine, dibutylstearylphosphine, tribenzylphosphine, cyclohexyldibutylphosphine, tricyclohexylphosphine, and the like. A convenient phosphine is tricyclohexylphosphine.

The R groups may be unsubstituted or substituted with oxygen, sulfur or nitrogen containing groups which do not unduly interfere with the reaction.

The mole ratio of hydrogen to carbon monoxide may be from 5:1 to 1:5; the preferred mole ratio is from about 2:1 to about 3:1. Generally the selectivity of the reaction to ethanol increases with the increase in mole ratio.

The cobalt, ruthenium, iodide, phosphine catalyst system is present in a catalytically effective amount, sufficient to catalyze the reaction, preferably from 1 to 20 weight percent, most preferably from 8 to 12 weight percent, based on the amount of methanol present.

The mole ratio of cobalt to methanol can be from 1:5 to 1:50,000, preferably from 1:50 to 1:500.

The mole ratio of cobalt to ruthenium can be from 1:0.003 to 1:3, preferably from 1:0.03 to 1:0.3.

The mole ratio of cobalt to phosphine compound can be from 1:0.1 to 1:100 preferably from 1:1.5 to 1:10. It is desirable to have a higher mole ratio of phosphine to cobalt to aid in catalyst stability when higher hydrogen to carbon monoxide ratios are employed.

The mole ratio of phosphine compound to total halide can be from 1:0.001 to 1:250 preferably from 1:0.36 to 1:5. When the phosphine is tricyclohexyl phosphine the preferred range is from 1:1.5 to 1:2.5.

The mole ratio of cobalt to total halide can be from 1:0.1 to 1:25, preferably from 1:1 to 1:5.

The mole ratio of cobalt: ruthenium: phosphine: halide is 1:0.003–3:0.1–100:0.1–25, preferably 1:0.03–0.3:1–.5–10:1–5.

This invention is the discovery that greater and greater amounts of phosphine ligand than heretofore believed possible can be added to the catalyst system, reaching concentrations heretofore unachievable and with the attendant enhancement of operating results, when the concentration of phosphine ligand is increased in conjunction with the concentration of halide, such that the mole ratio and concentration of phosphine ligand to halide remains within these critical limits. As is demonstrated in the examples which follow, increasing the ligand concentration such that the ligand to halide ratio is outside these critical limits, results in poorer performance. By use of the improved process of the invention the selectivity of the reaction to ethanol formation is significantly enhanced over that obtained by heretofore known methods. This is accomplished at relatively high rates of methanol conversion and under such conditions that the catalyst remains stable. Never before have the three parameters indicative of catalyst performance, i.e. stability, activity and selectivity, all been increased together.

The reaction can be run at a temperature of from 100° C. to 250° C., preferably from 150° C. to 200° C.

The reaction can be run at a pressure of from 1000 psig to 10,000 psig, preferably from 2000 psig to 6000 psig. The use of pressures higher than 10,000 psig, especially higher than 14–15,000 psig, leads to the formation of undesired mono- and polyhydric alcohols which may result in an overall carbon inefficiency to the desired product.

The time of the reaction will vary and is somewhat dependent on the reaction parameters employed and the individual reactants used.

In a typical embodiment of a laboratory scale batch process methanol is charged to a reactor with a catalyst containing a cobalt compound, an iodine compound, a ruthenium compound, and a phosphine ligand and the reactor is purged, charged with a hydrogen/carbon monoxide gas mixture sealed and heated until the desired reaction is completed. It is well known that commercially this process could be run continuously.

An additional advantage of this invention is that the excellent results are obtained without the need of an inert cosolvent such as octane, toluene, dioxane, and the like. This is of significant economic value.

The improved process and catalyst of this invention lead to significantly better catalyst performance and selectivity than have heretofore been achieved. By use of this invention one can now selectively increase the yield of ethanol from the reaction of methanol with hydrogen and carbon monoxide by increasing the concentration of phosphine ligand in the reaction mixture, thus allowing the use of higher hydrogen/carbon monoxide mole ratios, without the heretofore unavoidable deleterious effects on catalyst stability and selectivity. These advantageous results were unexpected and could not have been predicted.

It must also be noted that of the three indicators of catalyst performance, activity, selectivity and stability, selectivity is for practical considerations, of the grestest importance. This is because unreacted reactant can be recycled, and precipitated catalyst can be regenerated or discarded at no great cost, but reactant converted to undesired product is not only lost, but there are also created separation and other problems thereby putting significant economic strain on the system. Therefore, it is most desirable to maximize selectivity while maintaining acceptable levels of activity and stability. It is just this highly advantageous result which the improved process of this invention accomplishes.

The following examples serve to further illustrate the invention. In the tables the concentrations of cobalt, ruthenium, and iodine are the gram atom concentrations and not necessarily the concentration of their source compound.

EXAMPLE 1

In this example the following procedure was used for each of twelve runs. A glass lined 500 cc autoclave was charged with 50 ml of reagent grade methanol, cobalt acetate tetrahydrate, iodine, phosphine ligand and ruthenium trichloride or triruthenium dodecacarbonyl in the amounts indicated in Table 1. In runs 1–8 and 12 the ruthenium source was ruthenium trichloride and in runs 9–11 it was triruthenium dodecacarbonyl. In runs 2–11 the phosphine ligand employed was tricyclohexylphosphine and in run 12 it was triphenyl phosphine. The reactor was sealed and purged with carbon monoxide. The reaction was pressurized to 3000 psig with a gaseous mixture having a 2:1 molar ratio of hydrogen to carbon monoxide, sealed, and the reactor and its contents heated at the average temperature ($\pm 3°$ C.) reported in Table I for two hours during which the reactor was rocked to obtain thorough mixing. After this two hour period the reactor was cooled to 25°–30° C. and vented, and the liquid reaction mixture was isolated.

The reaction mixture was analyzed using a vapor phase gas chromatograph equipped with a thermal conductivity detector and a ⅛ inch by 6 foot column packed with 10 weight percent of polyethylene glycol, having an average molecular weight of about 20,000, on diatomaceous earth, comparing results from standard solutions; any cobalt metal formed was isolated and weighed. The results are reported in Table I. A cobalt metal rating of +2 corresponds to significant amounts of metal precipated out, +1 corresponds to a trace amount and—corresponds to no cobalt metal detected. The amount of cobalt precipitated is an indication of catalyst stability.

In Table I the values reported for methanol conversion percent and ethanol selectivity percent were determined from vapor phase chromatographic peak area analysis.

acceptable methanol conversion and ethanol selectivity but the cobalt catalyst was quite unstable.

Runs 2–6 exemplify introduction of and increasing the amount of phosphine ligand. In run 2 the catalyst is still unstable as the phosphine to cobalt ratio is less than the ratio found critical. The stability of the catalyst is increased in run 3 but the catalyst is still relatively unstable again due to the phosphine to cobalt ratio being outside the critical range. Runs 4, 5 and 12 show the high selectivity and good catalyst stability obtained when the reaction is carried out within the mole ratios of phosphine to halide and of phosphine to cobalt found critical by this invention. Run 6 demonstrates the poor results obtained when the phosphine to halide mole ratio exceeds the mole ratio found critical.

Run 7 shows the marked improvement obtained when the total halide concentration is increased relative to the concentration of phosphine ligand and Run 8 shows the excellent selectivity obtained when the concentration of phosphine ligand is increased over that of Run 7 such that the phosphine to cobalt ratio is within the critical range. Comparison of Runs 6 and 8, which both had a ligand/cobalt mole ratio of 3.33:1, dramatically illustrates the great advantage of increasing the concentration of ligand in conjunction with halide while maintaining a constant ligand to cobalt ratio, i.e. high conversion and selectivity with a stable catalyst is the result; and, as shown by Run 7, increasing the halide concentration alone is not as satisfactory, though some improvement is shown. Of prime importance, as a practical matter, is the maximization of selectivity at acceptable rates of conversion. This is because unconverted reactant can be recycled while reactant converted to undesired products is lost; furthermore this exacerbates the difficulty of product separation. Run 9 shows again the deleterious effect on conversion when ligand concentration in the reaction mixture is increased without also increasing halide concentration. Runs 10 and 11 further show the improvement in overall performance, even at high ligand/cobalt mole ratios, when ligand concentration is increased in conjunction with halide concentration.

EXAMPLE 2

In this example the following procedure was used for each of five runs. A stainless steel 150 ml reactor was charged with 75 ml of reagent grade methanol, a premix of cobalt acetate tetrahydrate, triruthenium dodecacarbonyl and iodine, and tricyclohexylphosphine as the

TABLE I

| Run # | Co (mmol) | Ru (mmol) | I (mmol) | Phosphine Ligand (mmol) | Mole Ratio Ligand/ Halide | Mole Ratio Ligand/ Cobalt | T °C. | MeOH Conversion % | EtOH Selectivity % | Co Metal |
|---|---|---|---|---|---|---|---|---|---|---|
| 1 | 4.8 | 0.44 | 4.0 | 0 | 0 | 0 | 181 | 43 | 62 | +2 |
| 2 | 4.8 | 0.44 | 4.0 | 2.0 | 0.38 | 0.42 | 180 | 47 | 65 | +2 |
| 3 | 4.8 | 0.44 | 4.0 | 6.0 | 1.12 | 1.25 | 181 | 42 | 76 | +1 |
| 4 | 4.8 | 0.44 | 4.0 | 8.0 | 1.50 | 1.67 | 183 | 36 | 78 | — |
| 5 | 4.8 | 0.44 | 4.0 | 12.0 | 2.26 | 2.50 | 180 | 31 | 80 | — |
| 6 | 4.8 | 0.44 | 4.0 | 16.0 | 3.00 | 3.33 | 180 | 6 | 37 | — |
| 7 | 4.8 | 0.44 | 8.0 | 6.0 | 0.64 | 1.25 | 183 | 57 | 69 | — |
| 8 | 4.8 | 0.44 | 8.0 | 16.0 | 1.71 | 3.33 | 181 | 43 | 80 | — |
| 9 | 8.0 | 0.66 | 10.0 | 30.0 | 3.00 | 3.75 | 180 | 8 | 42 | — |
| 10 | 4.8 | 0.48 | 5.4 | 12.0 | 2.22 | 2.50 | 187 | 43 | 78 | — |
| 11 | 4.8 | 0.48 | 9.5 | 16.0 | 1.68 | 3.33 | 182 | 45 | 78 | — |
| 12 | 4.8 | 0.44 | 8* | 8 | 1 | 1.67 | 182 | 25 | 73 | — |

*Using tetraethyl ammonium iodide.

Run 1 is an example of the reaction catalyzed without the phosphine ligand. The relatively high (2:1) mole ratio of hydrogen to carbon monoxide used allows for ligand in the amounts shown in Table II. The reactor was closed, purged, charged with a gaseous mixture of a 2:1 molar ratio of hydrogen to carbon monoxide, heated to 55° C., held at this temperature for 10 minutes, then pressurized to 3,500 psig with the same 2:1 gas mixture and then heated to 170° C. Agitation by means of a magnetic stirrer was begun, the temperature raised to 175° C. and the gas mixture was fed to the reactor as needed to maintain the pressure at about 6,000 psig. The reaction was allowed to continue until 10,000 psig of gas uptake had occurred or for a four hour period, whichever occurred first.

After the reaction was terminated the reactor and its contents were cooled to room temperature, the excess gas was vented and the reaction mixture was isolated. The reaction mixture was analyzed using a gas chromatograph and any cobalt metal formed was isolated. The results are reported in Table II.

Comparative Experiment A

For comparative purposes the procedure described in Example 1 was repeated in a series of twelve runs using a catalyst system which differed from the catalyst system useful in the process of this invention; in runs 1–4, 7, 8, 10, 11 and 12 there was no phosphine present and in runs 5, 6 the phosphine to cobalt mole ratio was below the range found critical; in run 9 the phosphine to halide ratio was outside the critical ratio define in my process. In all the runs the cobalt source was cobalt acetate and the ruthenium source was ruthenium trichloride. In runs 1–6 and 11 the iodide source was elemental iodine, in runs 7, 9 and 10 it was tetraethyl ammonium iodide, in run 8 it was manganese iodide and in run 12 it was tricyclohexyl methyl phosphonium iodide.

TABLE II

| Run # | Co mmol | Ru mmol | I mmol | Phosphine Ligand (mmol) | Mole Ratio Ligand/Halide | Mole Ratio Ligand/Cobalt | T °C. | MeOH Conversion % | EtOH Selectivity % | Co metal |
|---|---|---|---|---|---|---|---|---|---|---|
| 1 | 4.8 | .48 | 5.34 | 16.0 | 3.00 | 3.33 | 175 | 6 | 0 | — |
| 2 | 4.8 | .48 | 10.68 | 16.0 | 1.50 | 3.33 | 175 | 65 | 60 | — |
| 3 | 4.8 | .48 | 10.68 | 24.0 | 2.25 | 5.00 | 175 | 56 | 74 | — |
| 4 | 4.8 | .48 | 8.00 | 24.0 | 3.00 | 5.00 | 175 | 5 | 0 | — |
| 5 | 4.8 | .48 | 10.68 | 0 | 0 | 0 | 175 | 71 | 57 | +1 |

Run 1 demonstrates the very poor results obtained when the catalyst has a large concentration of ligand relative to cobalt (3.33:1) and halide (3:1). Runs 2 and 3 show the excellent results obtained when the halide concentration is increased such that the phosphine to halide ratio is within my defined critical range. By increasing the ligand concentration in conjunction with the halide concentration excellent results are obtained even at ligand/cobalt mole ratios previously shown to lead to very poor results. This phenomenon is best shown in run 3 where excellent results are obtained at a ligand/cobalt mole ratio of about 5/1; a ratio far higher than any heretofore achievable without the teachings of this invention. Runs 4 and 5 further demonstrate the difficulties of catalyst performance maximization and the poor results obtained when the process of this invention is not employed. Run 4 demonstrates the significantly lower conversion and selectivity which result when the ligand concentration is increased without also increasing the halide concentration. Run 5 is run with no ligand in the catalyst system; although there is good conversion and fair selectivity the catalyst exhibits instability.

In runs 5 and 6 the phosphine ligand employed was tricyclohexylphosphine; in run 9 it was triphenyl phosphine. These were the only runs in which a phosphine ligand was present. The concentrations of each and the reaction conditions are shown in Table III, as are the results.

TABLE III

| Run # | Co mmol | Ru mmol | I mmol | Phosphine Ligand (mmol) | Mole Ratio Ligand/Halide | Mole Ratio Ligand/Cobalt | T °C. | H₂/CO Mole Ratio | MeOH Conversion % | EtOH Selectivity % | Co Metal |
|---|---|---|---|---|---|---|---|---|---|---|---|
| 1 | .8 | 0 | 0.32 | 0 | 0 | 0 | 181 | 1:1 | 46 | 40 | +1 |
| 2 | .8 | 0 | 4 | 0 | 0 | 0 | 181 | 1:1 | 74 | 17 | — |
| 3 | .8 | .44 | 4 | 0 | 0 | 0 | 181 | 1:2 | 53 | 50 | — |
| 4 | .8 | .44 | 4 | 0 | 0 | 0 | 180 | 1:1 | 64 | 45 | +1 |
| 5 | .8 | .44 | 4 | 2 | 0.37 | 0.42 | 180 | 1:1 | 51 | 55 | — |
| 6 | .8 | .44 | 4 | 2 | 0.20 | 0.42 | 180 | 1:1 | 37 | 51 | — |
| 7 | .8 | .44 | 4 | 0 | 0 | 0 | 181 | 2:1 | 33 | 60 | +2 |
| 8 | .8 | .44 | 4 | 0 | 0 | 0 | 180 | 2:1 | 39 | 63 | +2 |
| 9 | .8 | .44 | 4 | 12 | 5 | 2.5 | 183 | 2:1 | 10.5 | 52 | — |
| 10 | .8 | .44 | 3 | 0 | 0 | 0 | 181 | 2:1 | 42 | 52 | — |
| 11 | .8 | .44 | 3 | 0 | 0 | 0 | 181 | 2:1 | 48 | 62 | — |
| 12 | .8 | .44 | 3 | 0 | 0 | 0 | 180 | 2:1 | 46 | 55 | — |

The results shown in Table III demonstrate the relatively poor results obtained when the improved process of this invention is not employed.

Run 1 shows the generally poor ethanol selectivity and catalyst stability obtained when the catalyst used in the improved process of this invention is not employed. Run 2 is a repeat of run 1 except that the concentration of halide is increased. There is an improvement in catalyst stability and methanol conversion but a sharp decline in the selectivity of the reaction to ethanol. In runs 1 and 2, ruthenium as well as phosphine were absent from the catalyst system. In runs 7, 10, 11 and 12 a similar trend was observed even though ruthenium was present. All six runs are outside the scope of this invention since they do not contain any phosphine; higher halide concentration is employed in runs 10, 11 and 12.

Run 3 was carried out with ruthenium present; only phosphine is absent. The mole ratio of hydrogen to carbon monoxide is quite low (1:2) and this results in good catalyst stability but the ethanol selectivity is only marginal. Run 4 is a repeat of run 3 except that the hydrogen to carbon monoxide mole ratio was increased to 1:1. The catalyst here has lost stability. Although increasing the hydrogen to carbon monoxide mole ratio generally increases the selectivity of the reaction to ethanol, here the selectivity to ethanol is slightly decreased. This is due to the changes that occurred to the composition of the homogeneous catalyst as a result of the loss of a portion of the cobalt component of the catalyst from solution induced by the increase in hydrogen to carbon monoxide mole ratio over that employed in run 3.

Runs 5, 6 and 9 show the use of all four components of the catalyst system of the process of this invention but not within the mole ratios found critical for good performance. Although the catalyst is stable the selectivity to ethanol is only fair, but it is slightly improved over that obtained in runs 3 and 4; methanol conversion would be acceptable in runs 5 and 6 but unacceptable in run 9.

Runs 7 and 8 demonstrate the effect of increased mole ratios of hydrogen to carbon monoxide on the reaction. The selectivity of the reaction is demonstrably increased but there is a drastically negative effect on catalyst stability and a perceptible decrease in catalyst activity.

This experiment series demonstrates one of the essential problems of carrying out any alcohol homologation reaction with a Group VIII metal catalyst i.e. the difficulty of simultaneously increasing the activity, selectivity and stability of the catalyst.

This is the achievement of the improved process of this invention. By comparing the results of the runs in the above Experiment A with the results of runs 8, 10, and 11 of Example 1 one can readily see that the improved process of this invention does in fact simultaneously improve the activity, selectivity and stability of the reaction of methanol, hydrogen and carbon monoxide to form ethanol. Furthermore, when comparing the results of runs 8, 10 and 11 of Example 1 with runs 5 and 6 of Experiment A, one can readily see that merely having the four components of the catalyst system, i.e. cobalt, ruthenium, iodide and phosphine, present, is not sufficient for good performance. There are required the specific, critical, mole ratios defined by the improved process of this invention, in order for one to achieve the highly advantageous results, as shown by applicant by his improved process.

What is claimed is:

1. In a substantially solvent free process of producing ethanol from the reaction of methanol, hydrogen and carbon monoxide wherein the reaction is catalyzed by cobalt, ruthenium, an iodine promoter, and a phosphine ligand of the formula

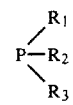

wherein P is phosphorus and $R_1$, $R_2$ and $R_3$ when taken individually are monovalent alkyl having from 1 to 20 carbon atoms; aryl, aralkyl or alkaryl having from 6 to 10 ring carbon atoms; or cycloalkyl having from 5 to 8 ring carbon atoms; and when any two taken together are a divalent alkylene having from 2 to 6 carbon atoms; the improvement comprising maintaining the phosphine to halide mole ratio at from 1:0.36 to 1:5 while the phosphine to cobalt mole ratio exceeds 1.5:1, whereby the activity, stability and selectivity to ethanol formation of the catalyst are increased.

2. The improved process as claimed in claim 1 wherein the said phosphine to halide mole ratio is about 1:0.45.

3. The improved process as claimed in claim 1 wherein the said phosphine to halide mole ratio is about 1:0.6.

4. The improved process as claimed in claim 1 wherein said phosphine to cobalt mole ratio is about 3.33:1.

5. The improved process as claimed in claim 1 wherein said phosphine to cobalt mole ratio is about 5:1.

6. The improved process as claimed in claim 1 wherein the mole ratio of hydrogen to carbon monoxide is from 5:1 to 1:5.

7. The improved process as claimed in claim 6 wherein the said mole ratio is about 2:1.

8. The improved process as claimed in claim 1 wherein the said cobalt compound is cobalt acetate tetrahydrate.

9. The improved process as claimed in claim 1 wherein said iodine promoter is elemental iodine.

10. The improved process as claimed in claim 1 wherein said ruthenium compound is ruthenium trichloride.

11. The improved process as claimed in claim 1 wherein said ruthenium compound is triruthenium dodecarcarbonyl.

12. The improved process as claimed in claim 1 wherein said phosphine ligand is tricyclohexylphosphine.

* * * * *

UNITED STATES PATENT AND TRADEMARK OFFICE
CERTIFICATE OF CORRECTION

PATENT NO. : 4,233,466
DATED : November 11, 1980
INVENTOR(S) : R.A. Fiato

It is certified that error appears in the above—identified patent and that said Letters Patent are hereby corrected as shown below:

In Table III, the column headings for the 8th through 12th column, reading from the left should read:

| T | Mole Ratio | MeOH | EtOH | Co |
|---|---|---|---|---|
| °C | $H_2/CO$ | Conversion % | Selectvity % | Metal |

In Table III, columns 6-12 for Run #2 reading from the left should read:

| 0 | 0 | 181 | 1:1 | 74 | 17 | -- |

Signed and Sealed this

Tenth Day of February 1981

[SEAL]

Attest:

RENE D. TEGTMEYER

Attesting Officer     Acting Commissioner of Patents and Trademarks